US009096685B2

(12) United States Patent
Sharma et al.

(10) Patent No.: US 9,096,685 B2
(45) Date of Patent: Aug. 4, 2015

(54) GENETIC MODIFICATION OF TARGETED REGIONS OF THE CARDIAC CONDUCTION SYSTEM

(75) Inventors: Vinod Sharma, Blaine, MN (US); Walter H. Olson, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 142 days.

(21) Appl. No.: 12/578,198

(22) Filed: Oct. 13, 2009

(65) Prior Publication Data

US 2010/0076063 A1 Mar. 25, 2010

Related U.S. Application Data

(60) Division of application No. 11/536,426, filed on Sep. 28, 2006, now abandoned, which is a continuation-in-part of application No. 10/424,080, filed on Apr. 25, 2003, now abandoned.

(51) Int. Cl.
| | |
|---|---|
| *A61K 31/70* | (2006.01) |
| *A61K 48/00* | (2006.01) |
| *C12N 15/00* | (2006.01) |
| *C07K 14/705* | (2006.01) |
| *A61K 38/17* | (2006.01) |
| *C07K 1/00* | (2006.01) |

(52) U.S. Cl.
CPC ............ *C07K 14/705* (2013.01); *A61K 38/177* (2013.01)

(58) Field of Classification Search
CPC .......................... C07K 14/705; A61K 38/177
USPC ............................................. 514/44; 424/93.2
See application file for complete search history.

(56) References Cited

U.S. PATENT DOCUMENTS

| | | | | |
|---|---|---|---|---|
| 5,103,821 | A | * | 4/1992 | King .................................. 607/9 |
| 5,417,717 | A | * | 5/1995 | Salo et al. ........................ 607/18 |
| 5,464,404 | A | * | 11/1995 | Abela et al. ..................... 606/15 |
| 5,991,660 | A | * | 11/1999 | Goyal ............................. 607/14 |
| 6,058,328 | A | * | 5/2000 | Levine et al. ................... 607/14 |
| 6,214,620 | B1 | | 4/2001 | Johns |
| 6,330,476 | B1 | * | 12/2001 | Ben-Haim et al. ................ 607/9 |
| 6,376,471 | B1 | | 4/2002 | Lawrence, III |
| 2002/0022259 | A1 | | 2/2002 | Lee |
| 2002/0095197 | A1 | * | 7/2002 | Lardo et al. ..................... 607/89 |
| 2002/0155101 | A1 | | 10/2002 | Donahue |
| 2004/0214182 | A1 | | 10/2004 | Sharma |

FOREIGN PATENT DOCUMENTS

| | | |
|---|---|---|
| WO | WO 98/02150 | 1/1998 |
| WO | WO 02/19966 | 3/2002 |
| WO | WO 02/33111 | 4/2002 |
| WO | WO 02/087419 | 7/2002 |
| WO | WO 02/098286 | 12/2002 |
| WO | WO 2005/062958 | 7/2005 |

OTHER PUBLICATIONS van Hemel et al. Long-term results of the corridor operation for atrial fibrillation. Br. Heart J. 71:170-176, 1994.*
Glenn et al., Gene Therapy to Develop a Genetically Engineered Cardiac Pacemaker, J. Cardiovascular Nursing 18:330-336, 2003.
Qu et al., Expression and Function of a Biological Pacemaker in Canine Heart; Circulation 107:1106-1109, 2003.
Katz, A.M., T-type Calcium Channels May Provide a Unique Target for Cardiovascular Therapy, European Heart Journal, 1 (Supp. H.), H-18-23 (1999).
Benson, D.A., et al., GenBank, Nuci, Acids Res., vol. 25, p. 1-6 (1997).
Clark et al., Cell Lines for the Production of Recombinant Adeno-Associated Virus, Human Gene Ther., vol. 6, p. 1329-1341 (1995).
Cribbs, L. L. et al., Cloning and Characterization of Alpha H from Human Heart, a Member of the T-Type Ca2+ Channel Gene Family, Cir. Res., vol. 83, p. 103-9 (1998).
Felgner, P., Cationic Liposome-Mediated Transfection with Lipofection Reagent, Methods in Molecular Biology, vol. 7, Gene Transfer and Expression Protocols, p. 81-89 (1991).
Graham, F. et al., Manipulation of Adenovirus Vectors, Methods in Molecular Biology, vol. 7, Gene Transfer and Expression Protocols, p. 109-206 (1991).
Guzman, R.J. et al., Efficient Gene Transfer into Myocardium by Direct Injection of Adenovirus Vectors, Circ. Res. vol. 73, No. 6, p. 1202-1207 (Dec. 1993).
Ishii, T.M. et al., Molecular Characterization of the Hyperpolorization-Activated Cation Channel in Rabbit Heart Sinoatrial Node, J. Biol. Chem., vol. 274, p. 12835-9 (1999).
Josephson, M.E., Electrophysiologic Investigation: General Concepts, Clinical Cardiac Electrophysiology: Techniques and Interpretations, p. 22-70 (1993).
Kagan, et al., The Dominant Negative LQT2 Mutation A516V Reduces Wildtype HERG Expression, J. Biol. Chem., vol. 275, p. 11241-11248 (2000).
Kirschlhof, C.J., et al., Evidence for the Presence of Electrotonic Depression of Pacemakers in the Rabbit Atrioventricular Node: The Effects of Uncoupling from the Surrounding Myocardium, Basic Res. Cardiol., vol. 83, p. 190-201 (1988).
LaPointe et al., Left Ventricular Targeting of Reporter Gene Expression in Vivo by Human BNP Promoter in an Adenoviral Vector, Am. J. Physiol., vol. 283, p. H1439-45 (2002).
Lee, J.H. et al., Cloning Expression of a Novel Member of the Low Voltage-Activated T-Type Calcium Channel Family, J. Neurosci. vol. 19, p. 1912-21 (1999).

(Continued)

Primary Examiner — Quang Nguyen
(74) Attorney, Agent, or Firm — Mueting, Raasch & Gebhardt, P.A.

(57) ABSTRACT

Disclosed are compositions, methods and systems for preventing or treating cardiac dysfunction, particularly cardiac pacing dysfunction by genetic modification of cells of targeted regions of the cardiac conduction system. In particular, a bio-pacemaker composition is delivered to cardiac cells to increase the intrinsic pacemaking rate of the cells, wherein the bio-pacemaker composition increases expression of a channel or subunit thereof that produces funny current and a T-type $Ca^{2+}$ channel or subunit thereof, and expresses one or more molecules that suppresses the expression of the wild type potassium channel.

18 Claims, 7 Drawing Sheets

(56) References Cited

OTHER PUBLICATIONS

Miake, J. et al., Biological Pacemaker Created by Gene Transfer, Nature, vol. 419, p. 132-3 (2002).

Schram, G. et al., Differential Distribution of Cardiac Ion Channel Expression as a Basis for Regional Specialization in Electrical Function, Circ. Res. vol. 90, p. 939-50 (May 17, 2002).

Schnepp et al., Highly Purified Recombinant Adeno-Associated Virus Vectors, Gene Therapy Protocol, $2^{nd}$ ed., p. 427-443 (2002).

Shorofsky, S.R., et al., Calcium Currents and Arrhythmias: Insights from Molecular Biology, A.J. Med. vol. 110, p. 127-40 (2001).

Vasquez, et al., Triplex-Directed Site-Specific Genome Modification, Gene Targeting Protocols, p. 183-200 (2000).

Ueda et al., Functional Characterization of a Trafficking-Defective HCN4 Mutation, D553N, Associated with Cardiac Arrhythmia, J. Biol. Chem.. vol. 279, p. 27194-27198 (2004).

Plotnikov et al., Biological Pacemaker Implanted in Canine Left Bundle Branch Provides Ventricular Escape Rhythms that have Physiologically Acceptable Rates, Cir. Amer. Heart Association, vol. 109, p. 506-512 (2004).

Bucchi et al., Wild-type and Mutant HCN Channels in a Tandem Biological-Electronic Cardiac Pacemaker, Circulation vol. 114, p. 992-999 (2006).

Rosen, et al., Recreating the Biological Pacemaker, the Antomical Record Part A, Discoveries in Molecular, Cellular and Evolutionary Biology, vol. 280, p. 1046-1052 (2004).

International Search Report, PCT/US07/07679, Jan. 31, 2008, 6 pages.

Ludwig et al., Two Pacemaker Channels from Human Heart with Profoundly Different Activation Kinetics, Embo Journal 18:2323-2329, 1999.

\* cited by examiner

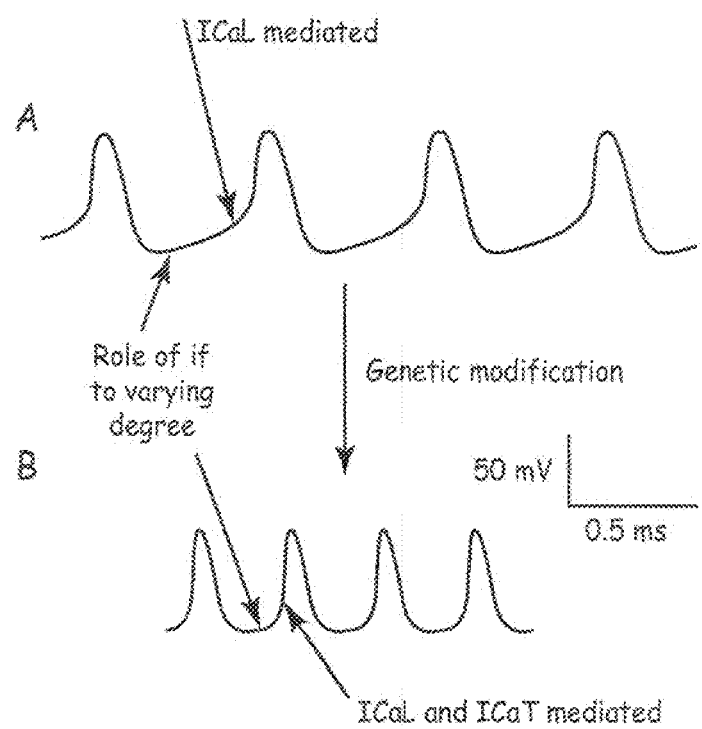

GENETIC MODIFICATION OF TARGETED REGIONS OF THE CARDIAC CONDUCTION SYSTEM

CROSS REFERENCE TO RELATED APPLICATIONS

This application is a divisional application of U.S. patent application Ser. No. 11/536,426 filed Sep. 28, 2006, now abandoned which is a continuation-in-part of U.S. patent application Ser. No. 10/424,080 filed Apr. 25, 2003, by Vinod Sharma and entitles "GENETIC MODIFICATION OF TARGETED REGIONS OF THE CARDIAC CONDUCTION SYSTEM", now abandoned.

FIELD OF THE INVENTION

The present invention relates to compositions, apparatus, and methods for providing curative therapy for cardiac dysfunction, and more particularly to biological systems and methods relating to implementing curative therapeutic agents and systems for arrhythmias and cardiac pacing dysfunction.

BACKGROUND

In a normal, healthy heart, cardiac contraction is initiated by the spontaneous excitation of the sinoatrial ("SA") node, located in the right atrium. The electrical impulse generated by the SA node travels to the atrioventricular ("AV") node where it is transmitted to the bundle of His and Purkinje network, which branches in many directions to facilitate simultaneous contraction of the left and right ventricles.

In certain disease states, the heart's ability to pace properly is compromised. Currently, such dysfunction is commonly rectified by the implantation of implantable pacemakers. While improving the lives of many patients, implantable pacemakers have a limited lifetime and hence, may expose a patient to multiple surgeries to replace the implantable pacemaker. Moreover, implantable pacemakers may not be capable of directly responding to the body's endogenous signaling that interacts with the SA node to increase or decrease its pacing rate.

Recently, biological methods of influencing the pacing rate of cardiac cells have been developed, including the use of various drugs and pharmaceutical compositions. Developments in genetic engineering have resulted in methods for genetically modifying cardiac cells to influence their intrinsic pacing rate. For example, U.S. Pat. No. 6,214,620 describes a method for suppressing excitability of ventricular cells by overexpressing (e.g. $K^+$ channels) or underexpressing certain ion channels (e.g. $Na^+$ and $Ca^{2+}$ channels). PCT Publication No. WO 02/087419 describes methods and systems for modulating electrical behavior of cardiac cells by genetic modification of inwardly rectifying $K^+$ channels ($I_{K1}$) in quiescent ventricular cells. PCT Publication No. WO 02/098286 describes methods for regulating pacemaker function of cardiac cells with HCN molecules (HCN 1, 2, 3, or 4 isoforms of the pacemaker current $I_f$).

A need remains, however, to implement a system of genetic modification therapy (biopacing) in cooperation with an implantable medical device (IMD) to insure successful curative therapy for cardiac dysfunction.

SUMMARY OF THE INVENTION

The present invention provides a biological pacemaker ("bio-pacemaker") that is capable of responding to physiological signals as well as facilitating and restoring synchronous contractions of the ventricles to thus mimic the function of a healthy heart. The bio-pacemaker is generated through the genetic modification of myocardial cells in a targeted region of the cardiac conduction system, through use of a bio-pacemaker composition.

In one aspect of the invention, a bio-pacemaker composition includes at least two coding sequences that encode one or more molecules in myocardial cells of the cardiac conduction system to increase the pacemaking rate of the cells. The coding sequences include a coding sequence that encodes a channel or subunit thereof that produces funny current, a coding sequence that encodes a T-type $Ca^{2+}$ channel or subunit thereof, and a coding sequence that encodes one or more molecules that suppresses the expression of the wild type potassium channel.

Preferably, cells of the conduction system are genetically modified using the bio-pacemaker composition to increase their pacing rate to a level resembling the intrinsic pacing rate of the SA nodal cells in a normal heart.

Preferably, the bio-pacemaker composition of the invention generates a bio-pacemaker in the cardiac conduction system cells by altering two or more characteristics of the cell to obtain the following: 1) increased inward $Ca^{2+}$ current, 2) increased inward funny current ($I_f$), and/or 3) decreased outward $K^+$ current.

Increased inward $Ca^{2+}$ current may be obtained by genetically modifying the target cells to overexpress T-type $Ca^{2+}$ channels or subunits thereof, and in one embodiment, the $\alpha_{1H}$ subunits of the T-type $Ca^{2+}$ channels are overexpressed.

Increased funny current ($I_f$) may be obtained by increasing the expression of funny current channels or subunits thereof. Preferably, the channels expressed are an isoform of the hyperpolarization-activated cation channel gene (HCN). The isoform chosen will be related to the mammalian species of cells being modified.

Decreased outward $K^+$ current may be obtained by delivering a bio-pacemaker composition to the target cells including a coding sequence designed to encode a molecule or protein that will suppress the expression of the wildtype potassium channels responsible for producing rapid potassium current ($I_{Kr}$). In one embodiment, the protein expressed is a dominant-negative form of the potassium channel protein.

In one further embodiment of the invention, a bio-pacemaker of the invention is used in combination with an implantable pacemaker. Specifically, the implantable pacemaker is programmed to work in cooperation with the genetically engineered bio-pacemaker to prevent cardiac dysfunction or to sense and monitor the pacemaking action of the genetically engineered bio-pacemaker. Further, the implantable pacemaker operates to pace the heart when the pacemaking action of the bio-pacemaker is not as expected. For example, two possible triggers for resorting to the implantable pacemaker are 1) a bio-pacemaker pacing rate less than a certain predetermined threshold value and 2) an intermittent but presumably normal function of the bio-pacemaker. Implantable pacemaker can be switched to the role of a primary pacemaker if one or more attempts to engineer a biological pacemaker fail in a patient.

In case the bio-pacemaker location is the AV node, the top portions of the AV node may be ablated to isolate the atria from the AV node. When the biopacemaker is located in the Purkinje network, the entire AV node may be ablated.

BRIEF DESCRIPTION OF THE DRAWINGS

FIGS. 4A and 4B show the action potential (AP) characteristics of the AV nodal cells (one location of the bio-pacemaker) before and after genetic modification in accordance with a method of this invention.

DETAILED DESCRIPTION OF THE PREFERRED EMBODIMENTS

The present invention relates to biological methods of increasing the intrinsic pacemaking rate of cells of the cardiac conduction system, such as the AV node of the heart by genetic modification of the cells.

In one embodiment, the invention relates to a composition that involves at least one or more genes such as that which is listed in Table 1. The gene encodes a subunit. Subunit is defined as the molecular protein that performs the actual ion channel function.

TABLE 1

| Channel subunits and GenBank accession numbers | |
|---|---|
| Gene/Subunit | Species [accession number] |
| HCN1 | Human [NM 021072]; Rat [NM 053375]; Mouse [NM 010408] |
| HCN2 | Human [NM 001194]; Rat [NM 053684]; Mouse [NM 008226]; Canine [XM 850140] |
| HCN3 | Human [NM 020897]; Rat [NM 053685]; Mouse [NM 008227] |
| HCN4 | Human [NM 005477]; Rat [NM 021658]; Mouse [XM 287905]; Canine [XM 535535]; Red Jungle Fowl [XM 425895] |
| T-type □1H subunit | Human [NM 00100507]; Mouse [NM 021415]; Canine [XM 537016] |
| T-type □1G subunit | Human [NM 198397]; Rat [NM 031601]; Mouse [NM 009783] |

In another embodiment, at least one or more of the species listed in Table 1 is a composition that is delivered to the AV node. The specie(s) modifies the AV node to make the AV node more similar to the SA node. In yet another embodiment, a patient is monitored after the specie(s) has been delivered to the AV node. A determination is made by, for example, a physician as to whether the patient is exhibiting an adverse immune response to the specie(s). For example, a doctor tests the patient's blood for antibodies generated in response to the specie(s) using an ex vivo system expressing the specie(s) delivered to the AV node of the patient. The physician can then select a second specie(s) to be introduced to the AV node if antibodies are generated based upon the first specie(s) delivered to the AV node.

An example of modeling data that supports various embodiments of the invention may be seen with respect Viswanathan P C, Coles J A Jr, Sharma V, Sigg D C "Recreating an artificial biological pacemaker: insights from a theoretical model," Heart Rhythm, 2006 July; 3(7):824-31. Epub 2006 Mar. 16, (http://www.ncbi.nlm.nih.gov/entrez/query.fcgi?CMD=search&DB=pubmed) the disclosure of which is incorporated by reference in its entirety herein.

Figure 1:
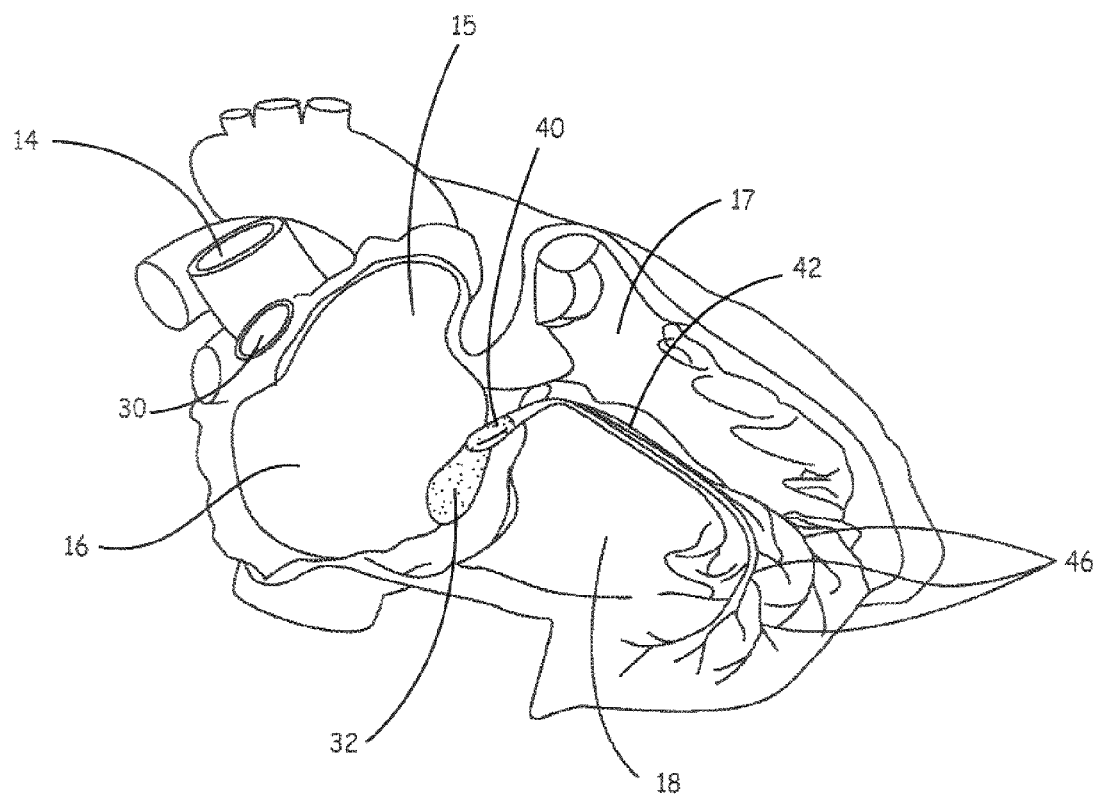
FIG. 1 is a diagram of a human heart.

FIG. 1 is a schematic diagram of a right side of a heart having an anterior-lateral wall peeled back to expose a portion of a heart's intrinsic conduction system and chambers of a right atrium 16 and a right ventricle ("RV") 18. Pertinent elements of the heart's intrinsic conduction system, illustrated, in FIG. 1, include a SA node 30, an AV node 32, a bundle of His 40, a right bundle branch 42, and Purkinje fibers 46. SA node 30 is shown at a junction between a superior vena cava 14 and right atrium ("RA") 16. An electrical impulse initiated at SA node 30 travels rapidly through RA 16 and a left atrium (not shown) to AV node 32. At AV node 32, the impulse slows to create a delay before passing on through a bundle of His 40, which branches, in an interventricular septum 17, into a right bundle branch 42 and a left bundle branch (not shown) and then, apically, into Purkinje fibers 46. Following the delay, the impulse travels rapidly throughout RV 18 and a left ventricle (not shown). Flow of the electrical impulse described herein creates an orderly sequence of atrial and ventricular contraction to efficiently pump blood through the heart. When a portion of the heart's intrinsic conduction system becomes dysfunctional, efficient pumping is compromised.

Typically, a patient, whose SA node 30 has become dysfunctional, may have an implantable pacemaker system implanted wherein lead electrodes are placed in an atrial appendage 15. The lead electrodes stimulate RA 16 downstream of dysfunctional SA node 30 and the stimulating pulse travels on to AV node 32, bundle of His 40, and Purkinje fibers 46 to restore physiological contraction of the heart. However, if a patient has a dysfunctional AV node 32, pacing in atrial appendage 15 will not be effective, since it is upstream of a block caused by the damage.

Pacing at the bundle of His 40 provides the advantage of utilizing the normal conduction system of the heart to carry out ventricular depolarizations. In other words, stimulation provided at the bundle of His will propagate rapidly to the entire heart via the right bundle 42, the left bundle (not shown), and the Purkinje fibers. This provides synchronized and efficient ventricular contraction, unlike pacing from the apex of the right ventricle where the electrical activity propagates at a slower rate because myocardial tissue is a slow conductor compared to the rapidly conducting Purkinje network.

Like cells of other excitable tissue in the body, cardiac cells allow a controlled flow of ions across the membranes. This ion movement across the cell membrane results in changes in transmembrane potential, which is a trigger for cell contraction. The heart cells can be categorized into several cell types (e.g. atrial, ventricular, etc.) and each cell type has its own characteristic variation in membrane potential. For example, ventricular cells have a resting potential of ~−85 mV. In response to an incoming depolarization wave front, these cells fire an action potential with a peak value of ~20 mV and then begin to repolarize, which takes ~350 ms to complete. In contrast, SA nodal cells do not have a stable resting potential and instead begin to spontaneously depolarize when their membrane potential reaches ~−50 mV. Cells, such as SA nodal cells, that do not have a stable resting transmembrane potential, but instead increase spontaneously to the threshold value, causing regenerative, repetitive depolarization, are said to have automacity.

Cardiac muscle cells are structurally connected to each other via small pore-like structures known as gap junctions, so that when a few cardiac cells depolarize, they act as a current source to adjacent cells causing them to depolarize as well; and these cells in turn relay the electrical charge to adjacent cells. Once depolarization begins within a mass of cardiac cells, it spreads rapidly by cell-to-cell conduction until the entire mass is depolarized causing a mass of cardiac cells to contract as a unit.

The cells in the SA node are specialized pacemaker cells and have the highest firing rate. Depolarization from these cells spreads across the atria. Since atrial muscle cells are not connected intimately with ventricular muscle cells, conduction does not spread directly to the ventricle. Instead, atrial depolarization enters the AV node, and after a brief delay, is passed on to the ventricles via the bundle of His and Purkinje network, initiating cellular depolarization along the endocardium. Depolarization then spreads by cell-to-cell conduction throughout the entire ventricular mass.

The SA node's unique cells include a combination of ion channels that endow it with its automacity. A review of the features of cardiac electrical function and description of the current understanding of the ionic and molecular basis, thereof, can be found in Schram et al., *Circulation Research*, May 17, 2002, pages 939-950, the teachings of which are herein incorporated by reference.

Some of the unique features of the SA node cells include the absence of $Na^+$ and inwardly rectifying $K^+$ ($I_{KI}$) channels. In the absence of sodium current, the upstroke of SA node action potential is primarily mediated by L-type $Ca^{2+}$ channels ($I_{CaL}$). SA node cells do not have a stable resting potential because of the lack of the and begin to depolarize immediately after the repolarization phase is complete. The maximum diastolic potential for SA node cells is approximately −50 mV compared to −78 mV and −85 mV for atrial and ventricular cells, respectively. The slow depolarization phase is mediated by activation of "funny current" ($I_f$) and T-type $Ca^{2+}$ channels and deactivation of slow and rapid potassium ($I_{Ks}$ and $I_{Kr}$, respectively). The rate of pacemaker discharge in the SA node in a normally functioning heart is approximately in the range of about 60 to 100 beats per minute.

In the diseased state, the ability of the SA node to properly pace the heart can be severely compromised. A method of the present invention includes genetically modifying the cells of the AV node to modify the electrophysiology and pacing rate to resemble more closely the electrophysiology and pacing rate of the specialized pacemaker cells of the SA node.

Figure 2:
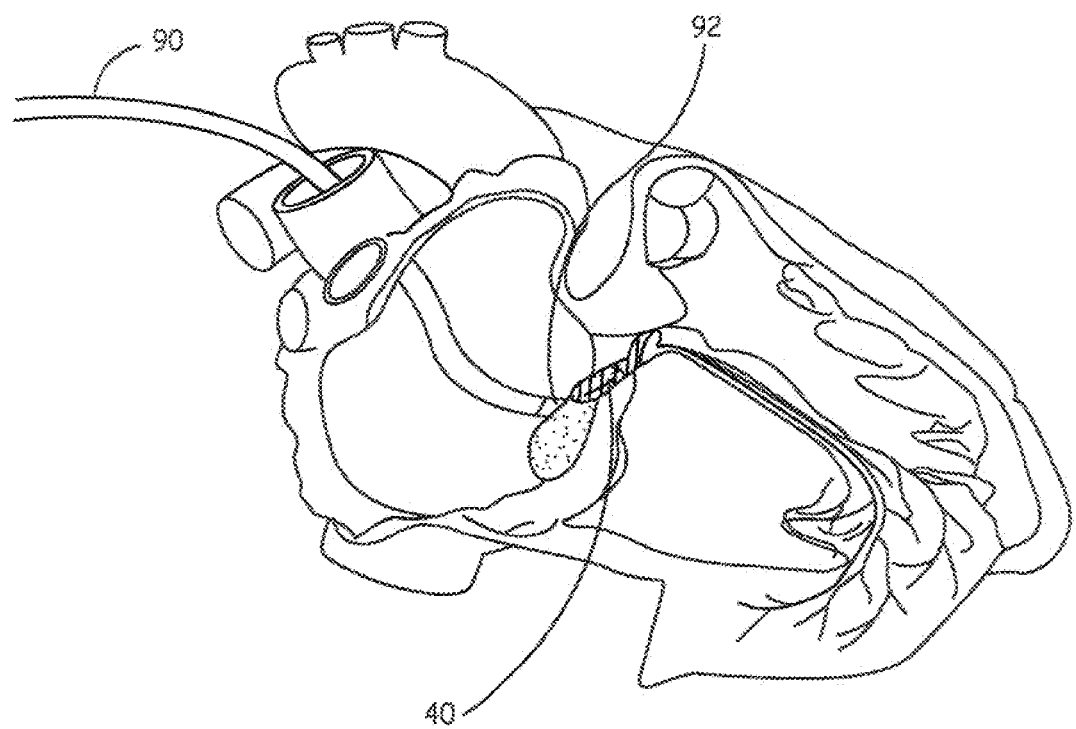
FIG. 2 is a schematic diagram of a right side of a heart, similar to FIG. 1, in which a guiding catheter is positioned for delivery of the genetic construct of the invention.

FIG. 2 is a schematic diagram of the right side of a heart; similar to that shown in FIG. 1, wherein a guide catheter 90 is positioned for delivery of the genetic construct of the invention. A venous access site (not shown) for catheter 90 may be in a cephalic or subclavian vein and means used for venous access are well known in the art, including the Seldinger technique performed with a standard percutaneous introducer kit. Guide catheter 90 includes a lumen (not shown) extending from a proximal end (not shown) to a distal end 92 that slideably receives delivery system 80. Guide catheter 90 may have an outer diameter between approximately 0.115 inches and 0.170 inches and is of a construction well known in the art. Distal end 92 of guide catheter 80 may include an electrode (not shown) for mapping electrical activity in order to direct distal end 92 to an implant site near bundle of His 40. Alternatively a separate mapping catheter may be used within lumen of guide catheter 90 to direct distal end 92 to an implant site near bundle of His 40, a method well known in the art.

Figure 3A:
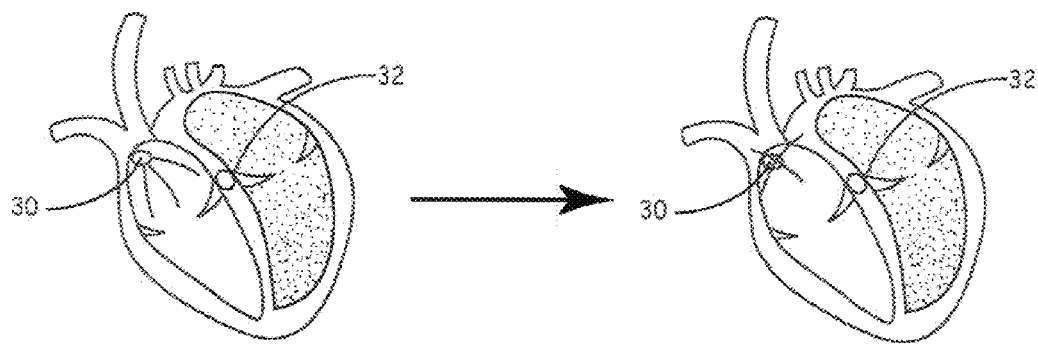
FIGS. 3A and 3B are schematics illustrating how an embodiment of the invention operates.
Figure 3B:
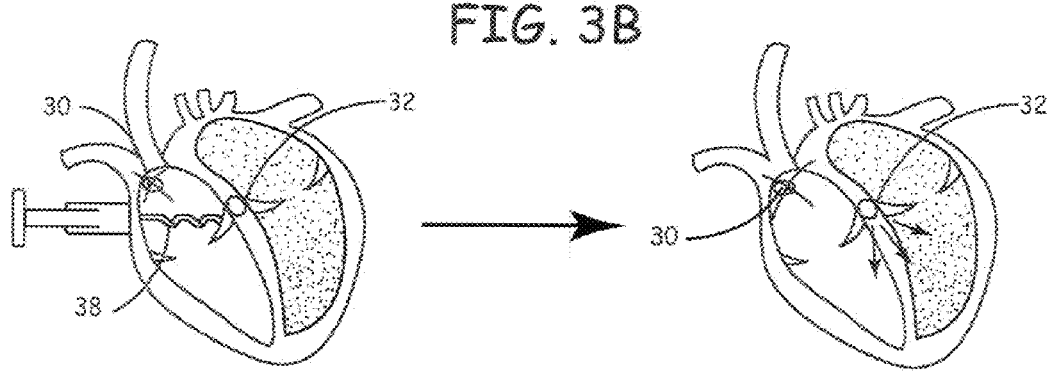

The schematics of FIGS. 3A and 3B illustrate an embodiment of the invention. FIG. 3A illustrates a heart with normal pacemaker function in the SA node 30 wherein the pacemaker function of the SA node is impaired. In a heart with dysfunctional SA node pacemaker function, the other structures in the heart with intrinsic pacemaking activity can take over the pacing function, but the heart rate generated will not be sufficient to support the normal circulation. FIG. 3B illustrates the delivery of a bio-pacemaker composition including a coding sequence in a genetic construct or vector 38 to the AV node portion of the conduction system. After the composition has been delivered to the host cell and modified gene expression has occurred, the AV node's electrophysiology will be restored to more closely resemble that of a normally functioning SA node.

In one embodiment of the invention, the top portions of the AV node may be ablated to isolate the atria from the AV node. This will serve three purposes: 1) enhance the firing rate of the AV node for a given expression of the exogenous channels; 2) prevent the AV node from being invaded by rapid atrial activity as can occur during atrial fibrillation and flutter; and 3) prevent the patient from experiencing uncomfortable junctional beats wherein atria and ventricles beat almost simultaneously.

An aspect of the present invention is to genetically modify the cells of the conduction system of a mammalian heart to increase the intrinsic pacing rate of such cells to resemble more closely the pacing rate of the SA node. In an embodiment of the invention, the intrinsic pacemaking rate of the cells is increased by delivering a bio-pacemaker composition of the invention to AV nodal cells to: 1) increase the inward $Ca^{2+}$ current, 2) increase the inward funny current ($I_f$), and/or 3) decrease the outward $K^+$ current in the modified cells.

The cells of the conduction system can be modified to maximize the transformation of these cells into the primary pacemaker and to increase their intrinsic pacing rate to a level resembling that of the SA node. Desirably, the intrinsic pacing rate of the modified cells is increased to a level substantially identical to that of the SA node. As used herein, "resembling" or "resembles" means that the pacing rate of the modified cells is increased to a level of at least about 85% of the pacing rate of the SA node cells for a particular patient when the heart is functioning normally and "substantially identical" means that the pacing rate of the modified cells is increased to a level of at least about 95% of the pacing rate of the SA node cells for the patient when the SA node of the heart is functioning normally.

The terms "encodes", "encoding", "coding sequence", and similar terms as used herein, refer to a nucleic acid sequence that is transcribed (in the case of DNA) and translated (in the case of mRNA) into a polypeptide in vitro or in vivo when place under control of the appropriate regulatory sequences.

In one embodiment of the invention, the cells of the conduction system may be genetically modified to increase the inward $Ca^{2+}$ current by delivering a genetic construct including one or more coding sequences to these cells. As a specific example, for the AV node the genetic construct includes a coding sequence encoding a T-type $Ca^{2+}$ channel resulting in increased expression (overexpression) of the T-type $Ca^{2+}$ channels thereby facilitating the depolarization of AV nodal cells and increasing their intrinsic pacing rate. In another embodiment, the genetic construct includes a coding sequence of a subunit of the T-type $Ca^{2+}$ channel and in one embodiment; the subunit is the $\alpha_{1H}$ subunit of the T-type $Ca^{2+}$ channel.

According to another embodiment, the cells of the conduction system are genetically modified to increase the funny current ($I_f$) by delivering a genetic construct including a coding sequence that encodes a channel producing the funny current. One such coding sequence is the hyperpolarization-activated cation channel gene (HCN) or a portion thereof. One or more isoforms of HCN may be used in the method of the invention. Four isoforms of the HCN family, HCN1, HCN2, HCN3, and HCN4 have been identified. Recent studies suggest that the HCN4 isoform is the predominant subunit encoding for the cardiac funny current channel in the SA node. (See, e.g., "Molecular Characterization of the Hyperpolarization-activated Cation Channel in Rabbit Heart Sinoatrial Node," *J. Biol. Chem.* 274:12835-12839 (1999)).

In yet another embodiment of the invention, the outward $K^+$ current of cardiac cells of the cardiac conduction system is decreased by suppressing the expression of the outward rectifying rapid potassium channel ($I_{Kr}$). Deactivation of $I_{Kr}$ during late phase repolarization facilitates depolarization of the SA node cells. SA node cells express both the rapid and slow $K^+$ channel with the rapid form predominating. The expression of $K^+$ channels varies in the conduction system. As a specific example, AV node cells express significantly higher levels of $I_{Kr}$. Without being bound by theory, it is predicted that these increased levels retard the subsequent depolarization that gives rise to an action potential thereby slowing the pacemaking rate of the AV node. Therefore, in accordance with another aspect of the invention, AV node cells are modified so that they express lower amounts of $I_{Kr}$, similar to the SA node or the conduction of each channel is lowered using genetic manipulation. The $I_{Kr}$ channel is comprised of subunits that coassemble to form $I_{Kr}$. One or more mutations of the pore forming □subunit encoded by HERG or the channel modulating subunit encoded by MiRP1 can potentially lower channel conductance.

According to another embodiment of the invention, the cells of the conduction system (e.g. AV node) are subject to one or more of the following modifications 1) overexpress T-type $Ca^{2+}$ channels 2) overexpress channels producing funny current ($I_f$) and 3) suppress wildtype potassium channel current. These channel modifications are preferably performed to an extent that the resulting electrophysiology of the AV node closely resembles that of the SA node. The modifications could be performed simultaneously or sequentially.

FIGS. 4A and 4B illustrate the effect of genetic alteration of the pacing rate of the AV node in the conduction system obtained with modification of these electrophysiological characteristics. As shown in FIG. 4A, in the wild type AV node, the L-type Ca2+ channel mediates depolarization. However, as shown in FIG. 48, after genetic modification using the method of the present invention relating to the delivery of one or more genetic constructs including a coding sequence that encodes the funny current channel and a T-type $Ca^{2+}$ channels, depolarization is mediated by both the L-type $Ca^{2+}$ and T-type $Ca^{2+}$ channels and the firing rate of the AV node is increased to the level of the SA node.

Figure 5A:
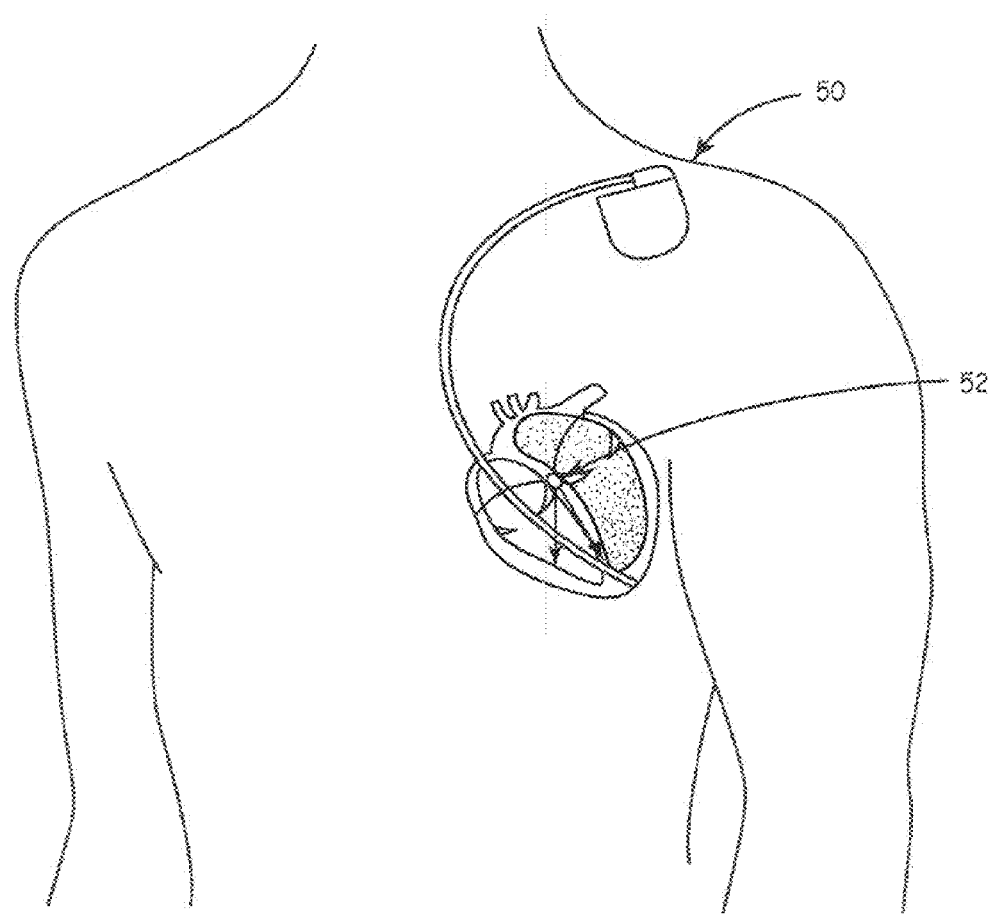
FIG. 5A illustrates the use of a small implantable backup pacemaker working in cooperation with the bio-pacemaker of the invention based on transforming the cells of the AV node in the conduction system.

Referring to FIG. 5A, an implantable pacemaker 50 is implemented with the bio-pacemaker 52 of the invention. In this embodiment, an implantable pacemaker 50, is implanted by methods well known in the art. The implantable pacemaker 50 may be adapted or programmed to serve several purposes. First, because cardiac disease onset is often sudden, the patient may require immediate pacemaker treatment. As is well known, the effects of gene or polynucleotide transfer may not be appreciated or effective for as long as several days. Thus, the implantable pacemaker may act as a bridge in the days following the genetic treatment of the present invention before full expression or suppression of channels is accomplished, as is depicted in the flow chart of FIG. 5B.

Figure 5B:
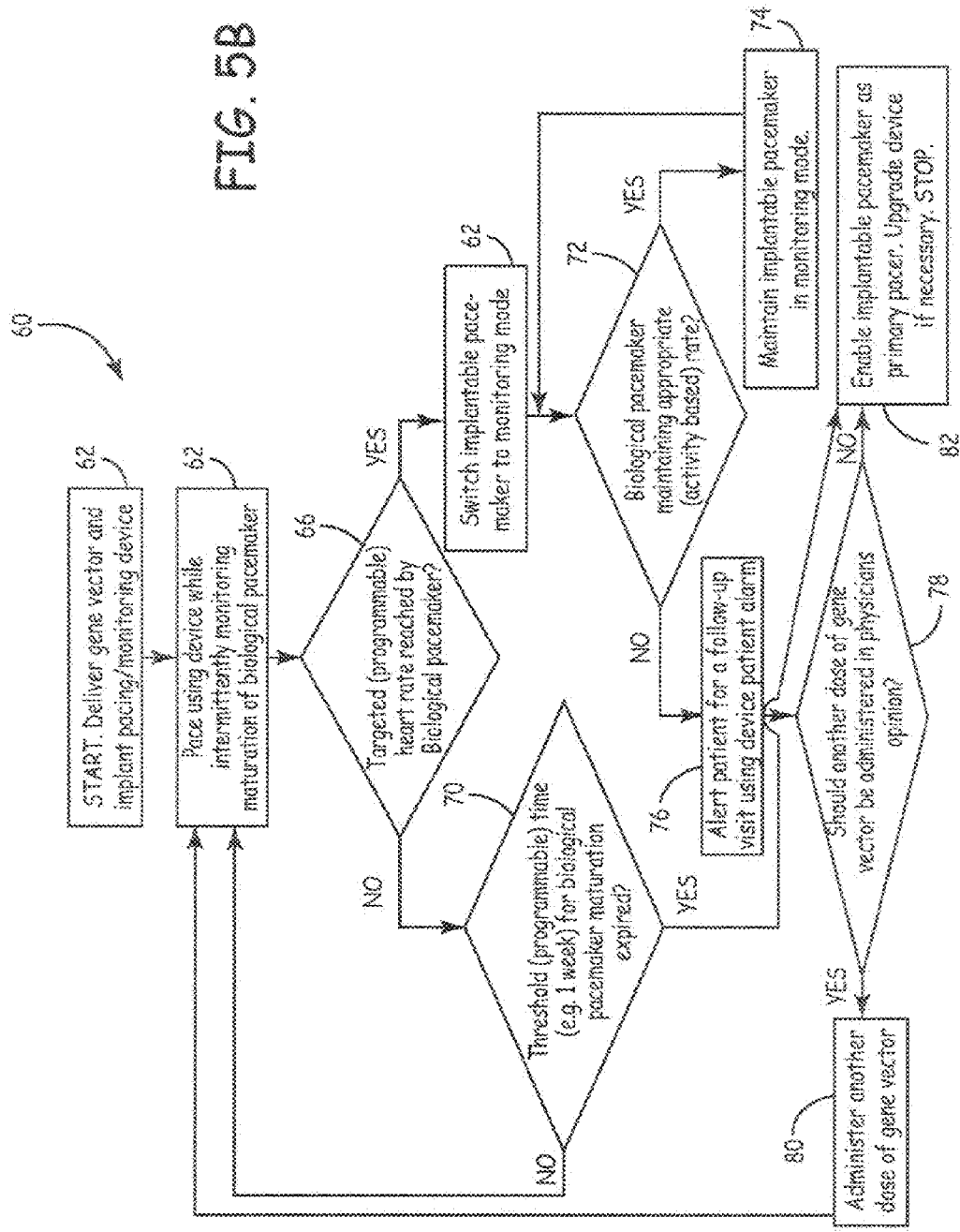
FIG. 5B is a logic flow diagram depicting the operational logic of the invention.

Referring to FIG. 5B, one aspect of the operational logic between the implantable pacemaker 50 and the bio-pacemaker 52 is shown. Computer implemented software logic system 60 includes logic step 62 where a gene vector is delivered to a targeted region of the cardiac conduction system and a pacemaker is implanted under logic step 62. Under logic step 64, the pacemaker is used to pace the patient's heart while intermittently monitoring the maturation of the biological pacemaker or the number of therapy occasions at which the gene vector has been delivered. Under decision step 66, when a targeted or programmable heart rate is reached by the biological pacemaker, the implantable medical device is switched to a monitoring mode under logic step 68. However, if the targeted heart rate has not been reached by the biological pacemaker, then under decision logic step 70, the time of the biological pacemaker maturation is checked whether it has expired. If the time has expired, then the logic proceeds to enable implantable pacemaker as a primary pacemaker under logic step 82. If, on the other hand, the threshold time for the biological pacemaker has not expired, the system reverts back to logic step 64 where pacing is done by the device while intermittently monitoring maturation of the biological pacemaker. Referring now to logic step 66, if the targeted heart rate is reached by the biological pacemaker, then under logic step 68, the implantable pacemaker is switched to only the monitoring operation of the biological pacemaker. Subsequently, under logic step 72, the biological pacemaker is checked to see whether it is maintaining the appropriate rate. If the appropriate pacing rate is maintained by the biological pacemaker, the implantable pacemaker is maintained in a monitoring mode, and in the alternative if the biological pacemaker is not keeping the appropriate rate, a patient alert is triggered to make the patient aware for a follow-up visit. Typically, the alert is communicated via device patient alarm, or other equivalent perceptible means. Further, under logic step 78, the system looks to see whether another dose of gene vector should be administered based upon a physician's opinion. If such a dose is confirmed, another dose of gene vector under logic step 80 is administered and the logic reverts back to logic step 64 to pace using the device while intermittently monitoring the maturation of the biological pacemaker. In the alternate, if the administration of another dose of gene vector is not advisable, the system reverts to logic step 82 where it would enable the implantable pacemaker to operate as the primary pacer. Further, the implantable pacemaker may act as backup to the bio-pacemaker of the present invention. In the event the bio-pacemaker fails, malfunctions, or a slowing in the pacing rate is sensed, the implantable pacemaker may be activated to take over the pacing function. Specifically, the implantable pacemaker may supplement the activity of the bio-pacemaker in the event the bio-pacemaker fails to produce sufficient stimulation. Finally, the implantable pacemaker alerts the patient to visit his/her physician if the pacemaking rate is not adequately keeping up with the patient activity. The data retrieved from the device can be used by the physician to asses and make decision as to whether the patient should be administered another dose of gene vector or genetic therapy should be abandoned and device itself should be used as the main pacer. Other purposes for employing an implantable pacemaker to supplement or to be used with the genetic modification of the AV node include chronic data management for diagnostic purposes and tracking and monitoring long term performance of the genetic pacemaker.

Modified cells may also be delivered to the AV node to genetically modify the myocardial cells to increase the intrinsic pacing rate of the cells. The modified cells may be the cells that can provide increased pacing rate and have been differentiated from stem cells such as embryonic or bone marrow stem cells.

Delivery of the bio-pacemaker composition of the invention can be carried out according to any method known in the art. It is only necessary that the composition reach a small portion of the cells that are targeted for gene manipulation (e.g. cells of the AV node). For example, a therapeutically effective amount of the bio-pacemaker composition may be injected into an artery that specifically perfuses the AV node. Alternatively the bio-pacemaker composition may be injected directly into the myocardium as described by R. J. Guzman et al., *Circ. Res.*, 73:1202-1207 (1993). The delivery step may further include increasing microvascular permeability using routine procedures, including delivering at least one permeability agent prior to or during delivery of the bio-pacemaker composition including one or more genetic construct. Perfusion protocols useful with the methods of the invention are generally sufficient to deliver the genetic construct to at least about 10% of cardiac myocytes in the mammal. Infusion volumes from about 0.5 to about 500 ml are useful. Methods for targeting non-viral vector genetic constructs to solid organs, for example, the heart, have been developed such as those described in U.S. Pat. No. 6,376,471, the teachings of which are hereby incorporated by reference.

Therapeutic methods of the invention comprise delivery of an effective amount of a genetic construct of the invention to the cells of the conduction system to increase the intrinsic pacing rate of these cells to resemble the pacing rate of the SA node cells when functioning normally. The delivery or administration may be accomplished by injection, catheter and other delivering means known in the art. A delivery system for delivering genetic material in a targeted area of the heart is described in PCT Publication No. WO 98/02150, assigned to the assignee of the present application, the teachings of which are herein incorporated by reference.

The genetic construct can be delivered into a cell by, for example, transfection or transduction procedures. Transfection and transduction refer to the acquisition by a cell of new genetic material by incorporation of added nucleic acid molecules. Transfection can occur by physical or chemical methods. Any transfection techniques are know to those of ordinary skill in the art including, without limitation, calcium phosphate DNA co-precipitation, DEAE-dextrin DNA transfection, electroporation, naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Foret virus vectors.

In the context of the present invention, methods for detecting modulation of the cells of the conduction system of the heart by electrophysiological assay methods relates to any conventional test used to determine the cardiac action potential characteristics, such as action potential duration (APD). An example of such a method related to performing such tests is disclosed by Josephson M E, *Clinical Cardiac Electrophysiology: Techniques and Interpretations*, Lea & Febiger. (1993), pp 22:70, the teachings of which are herein incorporated by reference. Briefly, a standard electrophysiological assay includes the following steps: providing a mammalian heart (in vivo or ex vivo), delivering to the heart a bio-pacemaker of the invention including a genetic construct or modified cells, transferring the genetic construct and/or modified cells into the heart under conditions which can allow expression of an encoded amino acid sequence; and detecting increase of at least one electrical property in the cells of the heart to which the genetic construct and/or modified cells were delivered, wherein at least one property is the pacing rate of the cells, relative to a baseline value. Baseline values will vary with respect to the particular target region chosen in the conduction system. Additionally, modulation of cardiac electrical properties obtained with the methods of the invention may be observed by performing a conventional electrocardiogram (ECG) before and after administration of the genetic construct of the invention and inspecting the ECG results. ECG patterns from a heart's electrical excitation have been well studied. Various methods are known for analyzing ECG records to measure changes in the electrical potential in the heart associated with the spread of depolarization and repolarization through the heart muscle.

In the invention, a genetic construct that includes a polynucleotide capable of increasing the expression of a particular ion channel or suppressing, in whole or in part, the expression or function of an ion channel may be made. Polynucleotides encoding the ion channel of choice can be made by traditional PCR-based amplification and known cloning techniques. Alternatively, a polynucleotide of the invention can be made by automated procedures that are well known in the art. A polynucleotide of the invention should include a start codon to initiate transcription and a stop codon to terminate translation.

Suitable polynucleotides for use with the invention can be obtained from a variety of public sources including, without limitation, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally, Benson, D. A. et al, *Nucl. Acids. Res.*, 25:1 (1997) for a description of GenBank. The particular polynucleotides useful with the present invention are readily obtained by accessing public information from GenBank.

Any DNA vector or delivery vehicle can be utilized to transfer the desired nucleotide sequence to the cells of the AV node. For example, $\alpha_{1H}$cDNA, HCN cDNA, or both may be cloned into a viral vector such as an adenoviral associated vector (AAV). Alternatively, other viral vectors such as, herpes vectors, and retroviral vectors such as lentiviral vectors may be employed. The type of viral vector selected is dependent on the target tissue and the length of the sequence to be delivered. For a discussion of viral vectors see *Gene Transfer and Expression Protocols*, Murray ed., pp. 109-206 (1991). Alternatively, non-viral delivery systems may be utilized. For example, liposome:DNA complexes, plasmid:liposome complexes, naked DNA, DNA-coated particles, or polymer based systems may be used to deliver the desired sequence to the cells. The above-mentioned delivery systems and protocols therefore can be found in *Gene Targeting Protocols*, Kmeic 2ed., pp. 1-35 (2002) and *Gene Transfer and Expression Protocols*, Vol. 7, Murray ed. P. pp. 81-89 (1991).

AAV vectors can be constructed using techniques well known in the art. Typically, the vector is constructed so as to provide operatively linked components of control elements. For example, a typical vector includes a transcriptional initiation region, a nucleotide sequence of the protein to be expressed, and a transcriptional termination region. Typically, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be chosen to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to another preferred embodiment, the vector contains the proximal human brain natriuretic brain (hBNP) promoter that functions as a cardiac-specific promoter. For details on construction of such a vector see LaPointe et al., "Left Ventricular Targeting of Reporter Gene Expression In Vivo by Human BNP Promoter in an Adenoviral Vector," *Am. J. Physiol. Heart Circ. Physiol.*, 283:H1439-45 (2002).

Vectors may also contain cardiac enhancers to increase the expression of the transgene in the targeted regions of the cardiac conduction system. Such enhancer elements may include the cardiac specific enhancer elements derived from Csx/Nkx2.5 regulatory regions disclosed in the published U.S. Patent Application 20020022259, the teachings of which are herein incorporated by reference.

Introducing the AAV vector into a suitable host, such as yeast, bacteria, or mammalian cells, using methods well known in the art, can produce AAV viral particles carrying the sequence of choice.

Thus, in the practice of the present invention, a construct can be produced that includes the coding sequence of the $\alpha_{1H}$ subunit of the T-type $Ca^{2+}$ channel or the HCN subunit of the funny current channel: When practicing the embodiment that calls for the introduction of both subunits, the sequences can be delivered simultaneously on a compound construct or may be co-delivered utilizing two separate constructs. The latter would allow for differential expression of the channels relative to each other by the selection of different promoters or administration of differing dosages.

A number of different constructs may be generated. For example, constructs for embodiments calling for expression of a single channel can be generated by cloning cDNA for a specific channel into a cloning plasmid. The constructs including coding sequence for a single channel are referred to as single gene constructs. Additionally, the single gene constructs can be used to titrate expression of the channels. For example, the level of expression of any particular introduced channel can be increased or decreased, relative to the expression level of another introduced channel by generating single gene constructs with differing promoters or administering differing dosages.

Targeted gene suppression can be accomplished by a number of techniques. In general, polynucleotides that interfere with expression of $I_{Kr}$ at the transcription or translation level may be administered to cells of the AV node. For example, a polynucleotide that encodes for a dominant negative form of the $I_{Kr}$ channel, may function as a decoy, or may sterically block transcription by triplex formation. Alternatively, antisense approaches may be employed.

A polynucleotide encoding a dominant negative form of the $I_{Kr}$ may be administered to cells of the AV node by techniques already described herein. Multimeric proteins are particularly amendable to this technique. Dominant negatives act to decrease levels of a particular protein by interfering with the assembly or function of the wild type protein. Preferably, the dominant negative is specific to targeted gene so that the function of other proteins is not altered.

Dominant negative gene suppression is achieved by introducing mutations in the gene and expressing the gene in a cell expressing wild type protein. The mutations may be introduced by site-directed mutagenesis. Effective dominant negative mutations of the $I_{Kr}$ may include those directed to the pore region such that the channel's conductance is reduced. Alternatively, mutations can be introduced that inhibit the trafficking of the channels to the cell surface and thereby decrease the number of functional channels and effective channel (macro) conductance at the cell membrane. Any such mutations are designed not alter ionic specificity of the channel. Additional dominant mutations include the introduction of hydrophilic amino acids in hydrophobic transmembrane regions. Such alterations prevent the effective assembly of the channel into the cell membrane. Other mutations that result in protein misfolding may also be utilized.

A particular construct for use in the present invention is an $I_{Kr}$ construct with the LQT2 A516V mutation. This mutation has been shown to have a dominant negative effect early when mutant subunits assemble with wild type subunits. See Kagan et al., "The Dominant Negative LQT2 Mutation A516V Reduces Wildtype HERG Expression," *J. Biol. Chem.*, 275: 11241-11248 (2000). Thus, a vector including the mutated form may be introduced into the cells of the AV node by techniques already described.

Suppression of $I_{Kr}$ in the cells of the cardiac conduction system through a method of this invention can also be accomplished by the administration of oligonucleotides that act as a decoy for transcription factors for at least one of the subunits of the channel. Decoys function to suppress the expression of a gene by competing with native regulatory sequences. The oligonucleotide may be administered to the cells of the AV node by techniques well known in the art. The oligonucleotide should be specific for transcription factors that regulate genes encoding at least one the subunits of the channel.

The invention may also be practiced employing triple helix technology to suppress $I_{Kr}$ expression. Thus, a single strand oligonucleotide may be introduced to the cells of the targeted region of the cardiac conduction system (e.g. AV node). Suppression of a targeted gene is accomplished by inhibition of transcription via the formation of a triple helix structure comprised of the targeted double strand DNA sequence and the oligonucleotide. Potential triple helix sites may be identified using computer software to search targeted gene sequence with a minimum of 80% purine over a 15 basepair stretch. The oligonucleotide may be synthesized with 3" propanolamine to protect against 3' exonucleases present in cells. For a discussion of triple helix techniques see Vasquez et al. Triplex-directed site-specific genome modification. *Gene Targeting Protocols*, Kmiec 2ed., pp. 182-200 (2000).

In accordance with the invention, $I_{Kr}$ expression may also be suppressed using antisense techniques. Antisense therapeutics is based on the ability of an antisense sequence to bind to mRNA and block translation. Antisense oligonucleotides must have high specificity for the target gene to avoid disruption of other non-targeted gene expression. More preferably, antisense oligodeoxynucleotides directed against $I_{Kr}$ subunit genes are employed. Artificial antisense oligodeoxyribonucleotides are favored because they can be synthesized easily, are readily transferred to the cytoplasm of cardiac conduction system cells using liposomes, and resist nuclease activity.

The pacing rate of any cardiac cell type is the product of the composition of channels expressed by the cell as well as electrotonic influences exerted by neighboring cells. For example, evidence suggests that the atria exerts electrotonic influences on the AV node, thereby inhibiting its pacing rate. Thus, to be effective, proposed genetic modifications must take into account the wild type channel expression as well as influences exerted by neighboring cells.

In accordance with the above described aspect of the present invention, in case AV node is the targeted region of the conduction system, ablation of the upper region of the AV node may be carried out in conjunction with the genetic treatment and implantable pacemaker implantation. Ablation will serve three purposes: 1) Enhance the efficiency of the bio-pacemaker since it is believed that the atria exert electrotonic influences on the AV node; 2) Prevent junctional beats that while being benign can cause significant discomfort to the patient 3) Uncouple atria from the AV node in patients suffering from atrial fibrillation.

In accordance with still another aspect of the present invention, the genetic manipulations described here may be practiced on stem cells. The genetically modified stem cells can then be administered to the cells of the cardiac conduction system to elicit pacemaking activity. For example, cardiac myocardial cells derived from stem cells may be treated with the genetic procedures described herein and implanted into a region of the conduction system (e.g. AV node) with a catheter or by direct injection to the AV nodal tissue.

The invention will be further described with reference to the following non-limiting Examples. It will be apparent to those skilled in the art that many changes can be made in the embodiments described in the Examples without departing from the scope of the present invention. Thus, the scope of the present invention should not be limited to the embodiments described in this application, but only by the embodiments described by the language of the claims and the equivalents of those embodiments.

EXAMPLE 1

Increased Intrinsic Pacemaking Rate of Genetically Modified AV Node

Construction of rAAV Cloning Plasmids
Construct Generation

Figure 6:
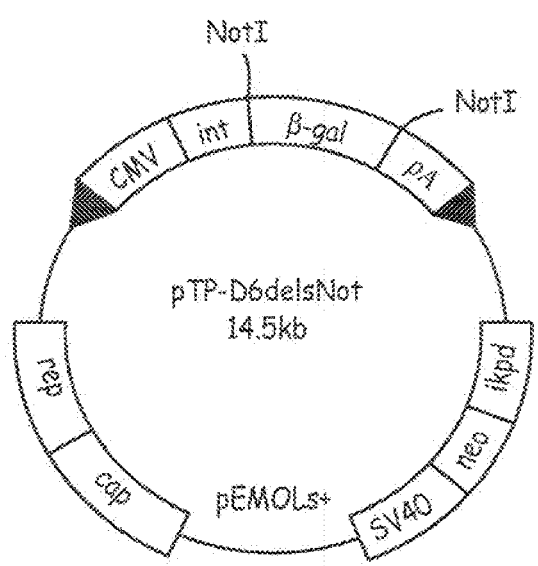
FIG. 6 is a schematic of the tripartite rAAV producer plasmid, pTP-D6deltaNot.

Genetic constructs (vectors) useful with the instant invention can be generated using traditional techniques as described by Schnepp and Clark in *Gene, Therapy Protocols*, Morgan 2ed., pp. 490-510 (2002). The T-type $Ca^{2+}$ channel is comprised of an $\alpha_{1H}$ subunit that has been cloned and its location mapped to human chromosome 16p13.3 (Cribbs et al., "Cloning and Characterization of $\alpha_{1H}$ From Human Heart, a Member of the T-type Calcium Channel Gene Family," *Cir. Res.*, 83:103-109 (1998). The sequence is deposited at GenBank accession No. AF051946. The role HCN4 plays in encoding the funny current channel is described, for example, in "Molecular Characterization of the Hyperpolarization-activated Cation Channel in Rabbit Heart Sinoatrial Node," *J. Biol. Chem.*, 274:12835-12839 (1999). The human HCN4 sequence is deposited at GenbBank accession No. NM005477.

cDNA of the $\alpha_{1H}$ subunit of the T-type $Ca^{2+}$ channel and HCN4 is cloned into the rAAV producer plasmid, pTP-D6deltaNot. This tripartite plasmid, shown in FIG. 6, includes AAV rep and cap genes, a neomycin resistance gene flanked by the SV40 promoter and thymidine kinase polyadenylation signal, and a gene expression cassette flanked by AAV inverted terminal repeats (ITRs) and includes the CMV promoter, SV40 large T-antigen intron, and polyadenylation signal, and beta galactosidase gene flanked by two unique NotI restriction sites. The cDNA replaces the beta galactosidase gene by excising the gene using NotI restriction enzymes and cloning in the above-mentioned cDNA. The resulting producer plasmid is used to produce rAAV particles. A person of ordinary skill in the art will know how similar constructs may be generated using different promoters. For example, a rAAV producer plasmid containing alternate promoters may be utilized.

The producer plasmid containing the coding sequence of the $\alpha_{1H}$ subunit of the T-type $Ca^{2+}$ channel and HCN4 is amplified by transformation of DH5-alpha *E. coli* and produces colonies that are screened by neomycin resistance. Producer plasmid is then isolated from resistant colonies and co-transfected with wild type adenovirus 5 (E1 deleted) into HeLA host cells. (for a discussion of the use of HeLA cells to produce rAAV particles see Clark et al., "Cell Lines for the Production of Recombinant Adeno-Associated Virus," *Human Gene Ther.* 6:1329-1341 (1995). Host cells containing the vector are purified using ammonium sulfate followed by double cesium banding. The bands containing the viral particle are isolated from the cesium chloride preparation and dialysis into Tris buffer.

AV nodal cells are modified by suppressing the expression of the rapid potassium channel using the dominant negative LQTR A516V of HERG. The dominant negative sequence is produced by synthesizing a synthetic oligonucleotide including the A516V substitution, using any known method such as the site directed mutagenesis system available in the Altered Sites® II Systems (Promega, Madison Wis.). This oligonucleotide is used as a primer to produce a plasmid containing the hybrid gene sequence. *E. coli* are transformed with the hybrid plasmid for amplification of the mutagenic gene.

In vivo Vector Administration

Adult guinea pigs are infected by perfusing a solution of saline with a viral concentration range of approximately $3 \times 10^{10}$ to $3 \times 10^{14}$ plaque forming units (PFU) directly into the AV nodal artery. Such a delivery method ensures that the vector reaches the cells of the AV node. After 4 days to allow for expression of the T-type $Ca^{2+}$ channels and the funny current channel, the modified AV mode activity is confirmed by transiently suppressing the interconnection between the atria and AV node using a cryoablation catheter to temporarily ablate the AV node and monitoring the ventricular rate using ECG procedures.

A catheter is used to locate the triangle of Koch, the region in which the AV node is situated. The catheter is first advanced to bundle of His region and the position of the His is noted on a fluoroscopic image, or image acquired by an image guidance system (reference). In a similar way ostium of the coronary sinus (OCS) is marked. This demarcates approximate location of the triangle of Koch. The catheter is then located in the triangle of Koch region in a region right above the tricuspid valve annulus and a needle is protruded to the hollow lumen of the catheter. A viral vector is injected in a linear region all along the tricuspid valve annulus starting at the His and ending dose to the OCS. A viral vector is generally defined as a biologic construct to carry a gene of interest (i.e. target gene etc.). Each injection contains ~$1 \times 10^6$ to $1 \times 10^9$ pfu of viral vector. An electrophysiological study is done before and after the injections to measure electrophysiological parameters of the AV node, such as wenkebach rate, effective refractory period, and atrial pacing rate for 2:1 A to V conduction.

All patents and publications referenced herein are hereby incorporated by reference in their entireties. It will be understood that certain of the above-described structures, functions and operations of the above-described preferred embodiments are not necessary to practice the present invention and are included in the description simply for completeness of an exemplary embodiment or embodiments. In addition, it will be understood that specifically structures, functions and operations set forth in the above-referenced patents can be practiced in conjunction with the present invention, but they are not essential to its practice. It is therefore to be understood that within the scope of the appended claims, the invention may be practiced otherwise than as specifically described without actually departing from the spirit and scope of the present invention.

What is claimed is:

1. A method of providing a biological pacemaker in a heart with dysfunctional SA node pacemaker function, the method comprising:

introducing a gene to an atrioventricular (AV) node of a patient, wherein the gene is a hyperpolarization-activated cyclic nucleotide-gated (HCN) channel gene selected from the group consisting of HCN1, HCN2, HCN3, and HCN4; and ablating at least an upper portion of the atrium to isolate electrical impulses initiated in the sinoatrial (SA) node from traveling to the AV node.

2. The method of claim 1, wherein the gene is HCN4.

3. The method of claim 2, wherein the HCN4 gene is selected from the group consisting of Human HCN4, Rat HCN4, Mouse HCN4, Canine HCN4, and Red Jungle Fowl HCN4.

4. The method of claim 1, further comprising pacing the patient's heart with a pacemaker.

5. The method of claim 4, further comprising monitoring the patient's heart rate.

6. The method of claim 5, wherein the pacemaker paces the patient's heart when a predetermined heart rate has not been reached.

7. The method of claim 6, further comprising determining whether the target heart rate has been reached within a predetermined amount of time.

8. The method of claim 7, further comprising employing the pacemaker as the patient's primary pacemaker if the target heart rate has not been reached within the predetermined amount of time.

9. The method of claim 1, wherein the gene is HCN1.

10. The method of claim 9, wherein the HCN1 gene is selected from the group consisting of Human HCN1, Rat HCN1, and Mouse HCN1.

11. The method of claim 1, wherein the gene is HCN2.

12. The method of claim 11, wherein the HCN2 gene is selected from the group consisting of Human HCN2, Rat HCN2, Mouse HCN2 and Canine HCN2.

13. The method of claim 1, wherein the gene is HCN3.

14. The method of claim 13, wherein the HCN3 gene is selected from the group consisting of Human HCN3, Rat HCN3, and Mouse HCN3.

15. The method of claim 4, wherein the gene is HCN4.

16. The method of claim 15, wherein the HCN4 gene is selected from the group consisting of Human HCN4, Rat HCN4, Mouse HCN4, Canine HCN4, and Red Jungle Fowl HCN4.

17. The method of claim 1, wherein the resultant electrophysiology of the AV node resembles that of a normally functioning SA node.

18. The method of claim 1, wherein the intrinsic pacing rate of the AV node cells is increased to the pacing rate of normal SA node cells.

* * * * *